United States Patent [19]
Kousaka

[11] Patent Number: 5,935,150
[45] Date of Patent: Aug. 10, 1999

[54] BACKBONE STRAIGHTENING DEVICE

[76] Inventor: Katumi Kousaka, 4-6 Kanayamacho, Kawaguchi-si, Japan

[21] Appl. No.: 08/917,040

[22] Filed: Aug. 13, 1997

[30] Foreign Application Priority Data

Aug. 26, 1996 [JP] Japan ................................. 8-009287 U

[51] Int. Cl.⁶ ..................................................... A61F 5/00
[52] U.S. Cl. .............................. 606/240; 128/845; 5/630; 5/652; 248/346.03; 297/284.1; 601/134; 602/32
[58] Field of Search ................................ 5/632, 633, 652, 5/657, 630; 128/95.1, 945; 211/41.1; 248/146, 176.1, 177.1, 314, 346.03; 297/259.1, 284.1, 284.4, 284.5, 284.9, 445.1; 434/259; 482/10, 79, 91, 44, 142, 907; 600/594; 601/134–137, 39; 602/32; 606/201, 204, 237, 238, 240

[56] References Cited

U.S. PATENT DOCUMENTS

| | | | |
|---|---|---|---|
| 1,833,426 | 11/1931 | Knudsen | 606/240 |
| 2,300,781 | 11/1942 | Gilley | 211/41.1 |
| 4,233,966 | 11/1980 | Takahashi | 601/134 |
| 4,350,152 | 9/1982 | Strakowski | 5/630 |
| 4,475,542 | 10/1984 | Brossard | 606/240 |
| 5,452,728 | 9/1995 | Iams | 28/845 |
| 5,542,910 | 8/1996 | Oliver | 602/18 |
| 5,575,295 | 11/1996 | Khalsa et al. | 128/845 |
| 5,722,102 | 3/1998 | Summers | 5/630 |
| 5,792,085 | 8/1998 | Walters | 606/201 |
| 5,820,573 | 10/1998 | Ramos | 601/134 |
| 5,873,846 | 2/1999 | Meilus | 601/134 |

*Primary Examiner*—Richard J. Apley
*Assistant Examiner*—Victor K. Hwang
*Attorney, Agent, or Firm*—Frishauf, Holtz, Goodman, Langer & Chick, P.C.

[57] ABSTRACT

A backbone straightening device includes a base plate, a platform member firmly secured to the base plate, and a plurality of circular ring-shaped supporting members. The platform member has a vertical cavity and two obliquely angled cavities. The vertical cavity is formed in a generally central area on a top surface of the platform member and has a rectangular opening in plan view, and the two obliquely angled cavities are respectively formed on opposite sides of the vertical cavity. The plurality of circular ring-shaped supporting members each have a cross-shaped connecting member integrally connecting an inside diameter thereof, and the plurality of circular ring-shaped supporting members are removably fitted in the vertical cavity and in the tapered cavities such that the supporting members are exposed above the platform member and such that upper peripheral edges of the supporting members projecting from the obliquely angled cavities are in contact with upper peripheral edges of at least one of the supporting members which projects from the vertical cavity.

11 Claims, 2 Drawing Sheets

BACKBONE STRAIGHTENING DEVICE

BACKGROUND OF THE INVENTION

1. Field of the Invention

This invention relates to a backbone straightening device, and more particularly to a backbone straightening device for correctly straightening the backbone of a patient from the cervical vertebra to the coccyx, so that any abnormality in the body of the patient caused by displacement of the backbone can be corrected.

2. Prior Art

In general, the backbone consists of thirty-two to thirty-four vertebras. A spinal canal containing a spinal cord extends through the backbone. The vertebras constitute a nerve center system together with the brain. The vertebras are readily displaced from their normal positions when a man or a woman does not keep straight in daily life. This displacement of the vertebras prevents the normal function of nerve center system. As a consequence, surgical, internal or neurological adverse effects and abnormalities occur to the human body.

Heretofore, many attempts have been made to straighten the displaced backbone (i.e., vertebras). They include, for example, unique ways of pulling, pushing, or various gymnastic exercises. Those pulling or pushing methods or various gymnastic exercises are, in fact, partly successful but none of them can completely satisfy the requirement for correctly straightening the backbone. In addition, those methods and exercises often compel a physical burden or stress to the patient.

The present invention has been accomplished in view of the above-mentioned problems inherent in the prior art.

SUMMARY OF THE INVENTION

It is, therefore, an object of the present invention to provide a backbone straightening device which is capable of effectively straightening the backbone, i.e., vertebras, of a patient without incurring much physical burden or stress to the patient, thereby normalizing the nerve center system so that physical and mental abnormalities of the patient can be corrected.

To achieve the above object, according to the present invention, there is essentially provided a backbone straightening device comprising a base plate, and a platform member firmly secured to the base plate. The platform member has a vertical cavity and two obliquely angled cavities, the vertical cavity being formed in a generally central area on a top surface of the platform member and having a rectangular opening in plan view, and the two obliquely angled cavities being spacedly formed on opposite sides of the vertical cavity. A plurality of circular ring-shaped supporting members are removably fitted in the vertical cavity and in the obliquely angled cavities with the remaining halves of the supporting members exposed above the platform member. Each of the supporting members has a cross-shaped connecting member integrally connecting the inside diameter of the supporting members, and upper peripheral edges of the supporting members projecting from the obliquely angled cavities are in contact with upper peripheral edges of the supporting member(s) projecting from the vertical cavity.

It is preferred that two of the supporting members are removably fitted in the vertical cavity in superposed relation.

It is also preferred that the obliquely angled cavities are formed on opposite sides of the vertical cavity at a same angle and at a same interval, with obliquely angled cavities inclined towards each other.

The supporting members may be each made of ceramic.

The supporting members are preferably each about 9 mm in thickness.

Since the backbone straightening device according to the present invention is constructed in a manner as mentioned above, when a patient lays himself or herself down on the device with the displaced vertebras from the cervical vertebra to the coccyx supported on the projecting tops of the supporting members of the device, the displaced vertebras can be restored to their original positions by the patient's own weight, in a natural manner and without any accompanying uncomfortable acute stimulation. Moreover, since the device of the present invention is constructed in the manner as mentioned above, the load caused by the patient's own weight can be vector-wise favorably dispersed. Therefore, the device is hardly susceptible to breakage and is easy to handle.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE EMBODIMENT

One preferred embodiment of the present invention will now be described with reference to the accompanying drawings.

Figure 1:
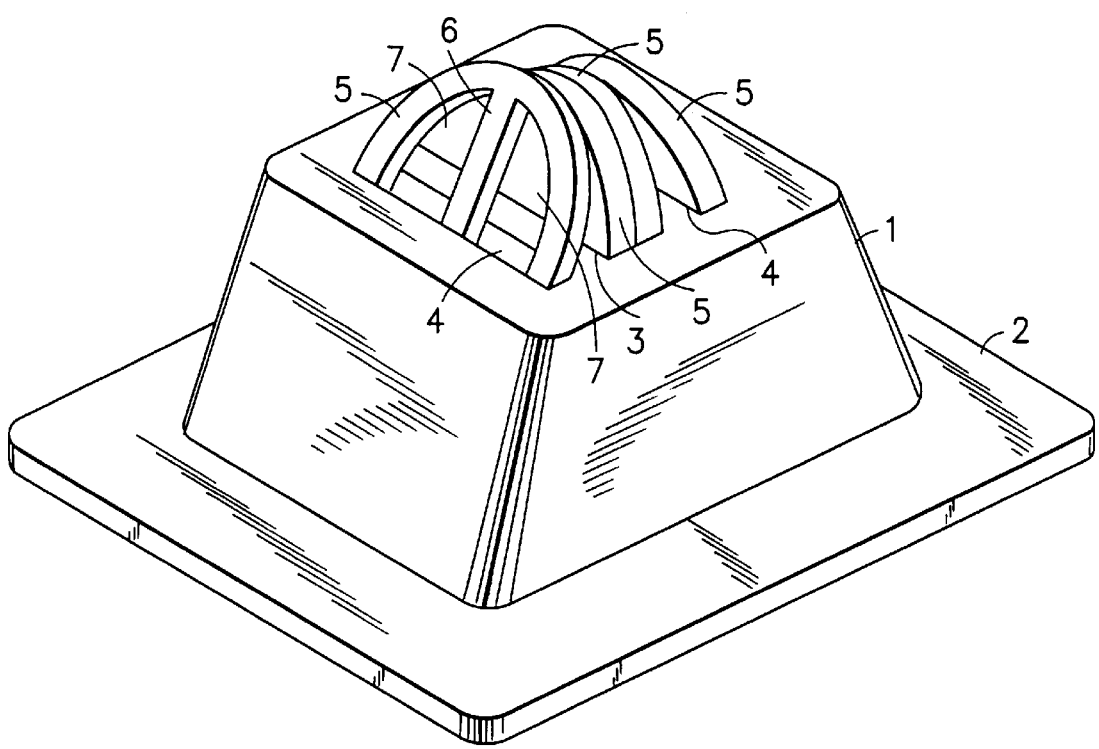
FIG. 1 is a perspective view of a backbone straightening device according to one embodiment of the present invention.
Figure 2:
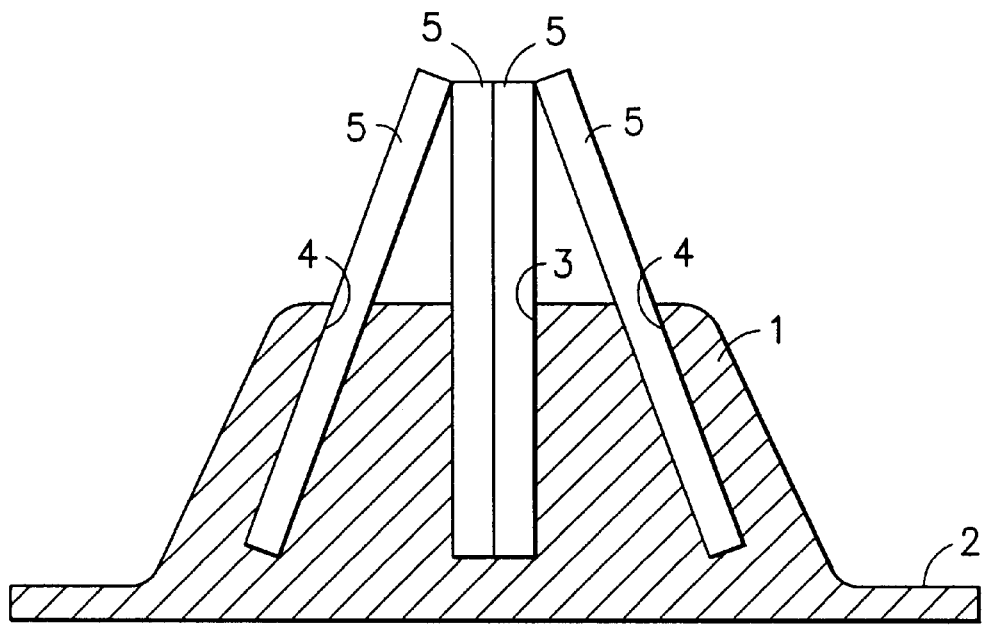
FIG. 2 is a vertical sectional view thereof.
Figure 3:
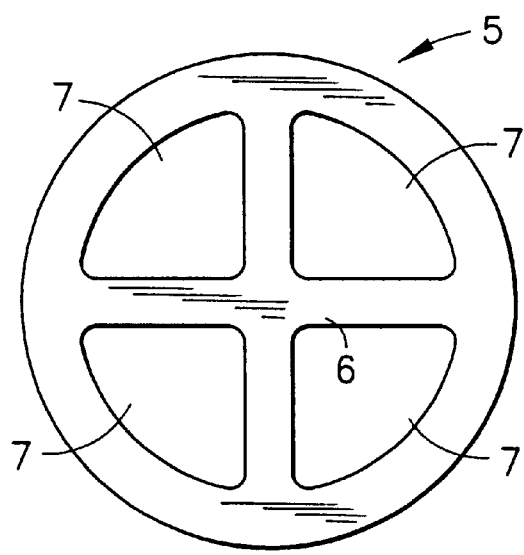
FIG. 3 is a front view of a supporting member.

In the drawings, reference numeral 1 denotes a platform member made of wood. It should be noted that although the platform member 1 of this embodiment is made of wood, it may be made of any other suitable material. The platform member 1 has a generally conical configuration, as a whole (see FIG. 1). The platform member 1 is firmly secured to the center of a base plate 2 which may be made of a cork material or any other suitable material.

A vertical cavity 3 having a comparatively wide generally rectangular opening in plan view is formed in a top surface of the platform member 1 along the outer contour of the platform member. Obliquely angled cavities 4, 4 each having a comparatively narrow generally rectangular opening in plan view are likewise formed in the top surface of the platform member 1 on opposite sides of the vertical cavity 3 and in equally spaced parallel relation to the vertical cavity 3. An angle of the cavities 4, 4 is preferably 29 degrees, and the cavities 4, 4 are inclined towards each other.

Two supporting members 5, 5 are removably fitted in the vertical cavity 3 in superposed relation and with upper halves thereof exposed above the platform member 1. Similar supporting members 5 are each removably fitted in each of the cavities 4, 4 in the same fashion as the previously-mentioned supporting members 5, 5. Due to inclination of the cavities 4, 4, upper peripheral edges of the supporting members 5, 5 projecting from the cavities 4, 4 are in contact with upper peripheral edges of the support members 5, 5 projecting from the vertical cavities 3.

Each supporting member 5 is made of ceramic in this embodiment. However, the material of the supporting member 5 is not limited to ceramic. For example, the supporting member 5 may be molded from wood or plastic. The supporting member 5 is 9 mm in thickness in this embodiment. This thickness of 9 mm is selected because an appropriate pressure can be given to the backbone of the patient. Each supporting member 5 exhibits a circular ring-shaped configuration as a whole. Each supporting member 5 is integrally connected at its inside diameter by a cross-shaped connecting member 6. Accordingly, four through-holes 7, 7, 7, 7 each having a sector configuration are defined by the supporting member 5 and the connecting member 6. Each supporting member 5 can be held by hand and used as a unitary member. In this case, the cross-shaped connecting member 6 may be caught by fingers. By pressing or rolling on other parts of the patient's body than the backbone with the supporting member 5 held by hand, abnormalities to the bones of such parts as the head, the shoulder, the hand and foot, or twisting of such parts of the patient can be eased by comfortable stimulation from the supporting members 5.

With the backbone straightening device of the present invention thus constructed, the two supporting members 5, 5 are removably fitted in the vertical cavity 3 and the remaining supporting members 5, 5 are each removably fitted in the cavities 4, 4. Then, the patient lays himself or herself on the supporting members 5, 5, 5, 5 with the displaced part of the patient placed on the projecting tops of the supporting members. By doing so, the displaced vertebras of the patient are gradually restored to their original correct positions by his or her own weight, in a natural manner.

The backbone straightening device according to the present invention is constructed and used in the above-mentioned manner. Accordingly, the position of each displaced vertebra can be corrected in a natural manner and without incurring any undue physical burden to the patient. Also, with regard to the backbone straightening device itself, the load can be dispersed to the supporting members and the platform member. Accordingly, the device is hardly susceptible to breakage. Moreover, the device of the present invention is simpler in construction and easier to handle than conventional devices. In addition, since the manufacturing cost can be reduced, the device of the present invention can be supplied to the end users at a reasonable price.

Obviously, numerous modifications and variations of the present invention are possible in light of the above teachings. It is, therefore, understood that within the scope of the appended claims, the invention may be practiced otherwise than as specifically described herein.

What is claimed is:

1. A backbone straightening device comprising:
   a base plate;
   a platform member firmly secured to said base plate, said platform member having a vertical cavity and two obliquely angled cavities, said vertical cavity being formed in a generally central area on a top surface of said platform member and having a rectangular opening in plan view, and said two obliquely angled cavities being respectively formed on opposite sides of said vertical cavity; and
   a plurality of circular ring-shaped supporting members each having a cross-shaped connecting member integrally connecting an inside diameter thereof, said plurality of circular ring-shaped supporting members being removably fitted in said vertical cavity and in said tapered cavities such that said supporting members are exposed above said platform member and such that upper peripheral edges of said supporting members projecting from said obliquely angled cavities are in contact with upper peripheral edges of at least one said supporting member projecting from said vertical cavity.

2. A backbone straightening device according to claim 1, wherein two of said supporting members are removably fitted in said vertical cavity in superposed relation.

3. A backbone straightening device according to claim 2, wherein said obliquely angled cavities are inclined toward each other and are formed on opposite sides of said vertical cavity at a same angle and at a same interval with respect to said vertical cavity.

4. A backbone straightening device according to claim 2, wherein said supporting members are each made of a ceramic material.

5. A backbone straightening device according to claim 2, wherein said supporting members each have a thickness of about 9 mm.

6. A backbone straightening device according to claim 1, wherein said obliquely angled cavities are inclined toward each other and are formed on opposite sides of said vertical cavity at a same angle and at a same interval with respect to said vertical cavity.

7. A backbone straightening device according to claim 6, wherein said supporting members are each made of a ceramic material.

8. A backbone straightening device according to claim 6, wherein said supporting members each have a thickness of about 9 mm.

9. A backbone straightening device according to claim 1, wherein said supporting members are each made of a ceramic material.

10. A backbone straightening device according to claim 9, wherein said supporting members each have a thickness of about 9 mm.

11. A backbone straightening device according to claim 1, wherein said supporting members each have a thickness of about 9 mm.

* * * * *